United States Patent [19]

Kitagawa et al.

[11] Patent Number: 4,650,697
[45] Date of Patent: Mar. 17, 1987

[54] PROCESS OF MANUFACTURING OXYGEN SENSOR

[75] Inventors: Jiro Kitagawa, Kasugai; Shuichiro Oki, Aichi, both of Japan

[73] Assignee: NGK Insulators, Ltd., Japan

[21] Appl. No.: 797,870

[22] Filed: Nov. 14, 1985

[30] Foreign Application Priority Data

Nov. 16, 1984 [JP] Japan .................................. 59-242758

[51] Int. Cl.$^4$ ............................................. B05D 5/12
[52] U.S. Cl. .................................. 427/125; 427/126.2; 427/126.3; 427/422; 427/423; 427/427
[58] Field of Search ................... 427/125, 126.3, 126.2, 427/422, 423, 427

[56] References Cited

U.S. PATENT DOCUMENTS

| | | | |
|---|---|---|---|
| 4,296,148 | 10/1981 | Friesse | 427/125 |
| 4,297,192 | 10/1981 | Shinohara | 427/125 |
| 4,345,985 | 8/1982 | Tohda | 427/125 |

*Primary Examiner*—Richard Bueker
*Attorney, Agent, or Firm*—Parkhurst & Oliff

[57] ABSTRACT

A process of manufacturing an oxygen sensor having an oxygen sensing element which includes an oxygen-ion conductive solid electrolyte body, a plurality of electrodes on the solid electrolyte body, and a porous ceramic protective layer which covers the electrode disposed on the side of a measurement gas, to protect the electrode from direct exposure to the measurement gas. The process comprises a step of heat-treating at least a portion of the ceramic protective layer covering the electrode, in a reducing atmosphere. The heat-treatment improves an operating response of the sensor over the entire range of temperature of the measurement gas.

12 Claims, 2 Drawing Figures

PROCESS OF MANUFACTURING OXYGEN SENSOR

BACKGROUND OF THE INVENTION

1. Field of the Art

The present invention relates generally to a process of manufacturing an oxygen sensor, and more particularly to a process suitable for manufacturing an improved oxygen sensor which has a shorter operating response.

2. Related Art Statement

It has been known that a fired body of zirconium oxide (zirconia ceramic) stabilized for example by CaO, $Y_2O_3$ can be used as oxygen-ion conductive solid electrolyte. Such zirconia ceramic or other oxygen-ion conductive solid electrolyte materials have been utilized for oxygen sensors which operate according to the principle of an oxygen concentration cell, to detect the concentration of oxygen in a measurement gas in the form of an exhaust gas produced by an internal combustion engine as used in an automotive vehicle, so that an air-fuel ratio of an air-fuel mixture for the engine is controlled in response to the detected oxygen concentration of the exhaust gas.

An oxygen concentration sensor of the type indicated above comprises a tubular or planar body of zirconia ceramic having therein a longitudinal bore or passage which communicates with ambient air. The tubular or planar zirconia ceramic body is provided on its inner and outer surfaces with an inner and an outer electrode, for example, platinum electrodes having a porous structure, respectively. The inner electrode serves as a reference electrode which is exposed to the ambient air in the longitudinal bore or passage, i.e., exposed to a reference gas whose oxygen concentration is used as a reference. The outer electrode serves as a measuring electrode which is designed to be exposed to an exhaust gas to be sensed. An electromotive force induced between the reference and measuring electrodes due to a difference in oxygen concentration between the reference and exhaust gases is detected to determine the oxygen concentration of the exhaust gas.

In a known oxygen sensor, as discussed above, the oxygen-ion conductive solid electrolyte body and the electrodes formed on their surfaces constitute an oxygen sensing element, which is a major component of the oxygen sensor. For improved durability of the electrode of the sensing element which is exposed to the exhaust gas of a high temperature, this electrode is protected by a suitable porous ceramic coating layer, as disclosed in U.S. Pat. No. 3,645,875. Such a protective coating layer is formed with a flame or plasma spraying method, or other spray-coating methods.

In the oxygen sensor art discussed above, there is a recognition that various factors determine an operating response of an oxygen sensor, that is, a rate or speed of detecting an electromotive force which is induced in the sensor in response to a change in oxygen concentration (oxygen partial pressure) of the exhaust gas, more particularly, a speed at which the oxygen sensor obtains an electric signal (electromotive force) which indicates whether the exhaust gas emitted from an engine is a "rich-burned" exhaust gas or a "lean-burned" exhaust gas. The rich-burned exhaust gas is interpreted to means an exhaust gas which is produced as a result of combustion of a fuel-rich air-fuel mixture, which the lean-burned exhaust gas is interpreted to mean an exhaust gas which is produced in combustion of an air-rich air-fuel mixture. When the exhaust gas temperature is relatively low, the response of the oxygen sensor is determined by a catalytic activity of a metallic material used for the electrode, such as platinum. It is recognized that the response becomes shorter as the number of active points of catalyst on the electrode is increased. When the temperature of the exhaust gas is relatively high, the operating response of the oxygen sensor is determined by a rate of diffusion of the exhaust gas components through the ceramic coating layer and the electrode layer. It is recognized that the response speed is increased as a diffusion resistance of the coating and electrode layers is reduced. In light of the above observations, the electrode layer of platinum or other metal should have a sufficiently large specific surface area and at the same time should have a porous structure, in order to provide satisfactory levels of operating response over the entire range of temperature of the exhaust gas.

Different processes are known for forming electrodes of platinum or other metallic materials of a conventional oxygen sensor. For example, the electrodes are formed by plating, sputtering, thermal decomposition of salt, or firing of a paste applied in a desired form. However, the electrodes formed in any of such processes have been found unsatisfactory in terms of their effect on an operating response of the sensor over the entire range of temperature of the exhaust gas.

SUMMARY OF THE INVENTION

It is therefore an object of the present invention to provide an oxygen sensor which is improved in its operating response over the entire range of temperature of a measurement gas.

Another object of the invention is the provision of a process suitable for forming porous electrodes on a solid electrolyte body of the sensor so that the electrodes have a sufficiently large specific surface area.

According to the present invention, there is provided a process of manufacturing an oxygen sensor having an oxygen sensing element which includes an oxygen-ion conductive solid electrolyte body, a plurality of electrodes on the solid electrolyte body, and a porous ceramic coating layer which covers at least one of the electrodes which is dispersed on the side of a measurement gas, so that the above-indicated one of the electrodes is exposed to the measurement gas through the porous ceramic coating layer, the process comprising the steps of: forming the porous ceramic coating layer so as to cover at least the above-indicated at least one of the electrodes; and heat-treating at least a portion of the porous ceramic coating layer which covers the above-indicated at least one electrode, in a reducing atmosphere.

In the manufacturing process of the invention as described above, the heat-treatment of the porous ceramic coating layer covering at least one of the electrodes which is designed to be exposed to the measurement gas, is effected in the reducing atmosphere by heating the solid electrolyte body with the electrodes and the coating layer, by heating the oxygen sensing element including the solid electrolyte body with the electrodes and the coating layer, or by heating an assembly of the oxygen sensor including the oxygen sensing element. It was found that the heat-treatment of the porous ceramic coating layer was effective in improving the response of the oxygen sensor. The reason for the improvement in the response by application of the heat-treatment of the ceramic coating layer has not yet been completely analyzed and not been made sufficiently clear. However, the inventors of the present invention have the following presumption in this respect.

That is, it is presumed that the electrode formed on the oxygen-ion conductive solid electrolyte body is subject to a change in nature due to a certain thermal hysteresis which may occur while the solid electrolyte body is built in the oxygen sensing element, and while the sensing element is built in the oxygen sensor. In particular, it is noted that the electrode of platinum or other metal tends to be partially oxidized or fused or melted by the heat of molten particles of a ceramic material during plasma or flame spraying of the molten particles over the electrode to form the ceramic coating layer. It appears that the application of such heat from the high temperature molten ceramic coating material to the electrode may result in reducing the specific surface area and porosity of the layer of the electrode made of platinum or other metal which serves as a catalyst, thereby deteriorating the operating response of the oxygen sensor over the entire range of temperature of the exhaust gas.

According to the presumption of the inventors, on the other hand, the heat treatment according to the invention in the reducing atmosphere after the formation of the porous ceramic coating layer will cause the oxidized or fused portion of the electrode layer to be reduced or sintered. As a result, the specific surface area of the electrode is significantly increased to improve the response in a comparatively low temperature range of the exhaust gas. Simultaneously, the electrode layer is provided with a porous structure of finer minute pores having excellent gas permeability, which improves the response of the sensor in a comparatively high temperature range of the exhaust gas.

BRIEF DESCRIPTION OF THE DRAWING

The above and other objects, features and advantages of the present invention will be better understood from reading the following detailed description, when considered in conjunction with the accompanying drawings, in which.

DETAILED DESCRIPTION OF THE INVENTION

The oxygen-ion conductive solid electrolyte body of the oxygen sensor produced according to the invention may be made of a solid electrolyte material such as zirconium oxide (zirconia), which is stabilized by yttrium oxide (yttria), calcium oxide (calcia), or the like. With such solid electrolyte material, a tubular or planar body having a longitudinal reference-gas bore or passage is formed by suitable known methods such as a press-forming or a lamination method. This tubular or planar solid electrolyte body forms a major part of the oxygen sensing element of the oxygen sensor.

Subsequently, the thin layers of the electrodes are formed on the corresponding inner and outer surfaces of the solid electrolyte body. These electrode layers are made from an element selected from the platinum group which includes platinum, ruthenium, osmium, iridium, rhodium and palladium, or made from an electrical conducting material whose major component is selected from the platinum group. The electrode layers may be formed with a method selected from various known processes such as plating, sputtering, thermal decomposition of salt of the selected electrode metal, or applying a paste of the selected electrode metal and subsequently firing the paste. It was found that the present invention is effective particularly where the electrodes are formed in a plating process, since the plating technique gives the electrode a highly dense structure.

For increasing the adherence or bonding of the electrodes to the solid electrolyte body, the corresponding surfaces of the solid electrolyte body may be roughened by suitable means. Further, it is possible to apply a heat treatment to the solid electrolyte body, as needed, after the electrodes have been formed. While the foregoing description indicates that the electrodes are formed after the solid electrolyte body is formed, it is possible to simultaneously form the solid electrolyte body and the electrodes. For example, if a planar solid electrolyte body with electrodes is formed with a known lamination method, green layers of the electrodes are concurrently formed on a green sheet of the planar solid electrolyte body by screen-printing and subsequent firing steps.

As described above, a plurality of electrodes including a reference and a measuring electrode are formed on respective surfaces of a solid electrolyte body. Generally, one of the electrodes which is formed on the outer surface of the solid electrolyte body is assigned to serve as a measuring electrode which is exposed to a measurement gas such as an exhaust gas. Additionally, the electrode formed on the inner surface of the solid electrolyte body is designed to act as a reference electrode which is exposed to a reference gas whose oxygen concentration is used as a reference.

Figure 1:
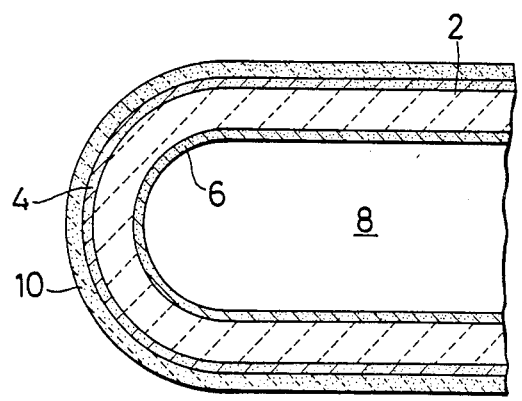
FIG. 1 is a fragmentary view in cross section of a sensing element using a tubular solid electrolyte body, showing an oxygen detecting portion at a closed end of the solid electrolyte body.
Figure 2:
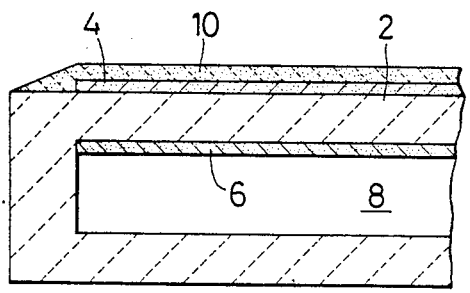
FIG. 2 is a similar view of a sensing element using a planar solid electrolyte body, showing an oxygen detecting portion at one longitudinal end of the solid electrolyte body.

Referring to FIGS. 1 and 2, reference numeral 2 designates a solid electrolyte body of a tubular or planar shape. On an outer and an inner surface of the solid electrolyte body 2, there are formed an outer measuring electrode 4, and an inner reference electrode 6, respectively. The outer measuring electrode 4 is disposed on the side of a measurement gas whose oxygen concentration is to be determined. The tubular or planar solid electrolyte body 2 has a longitudinal reference-gas bore or passage 8 which communicates at its open end with an ambient air. The inner reference electrode 6 is disposed so that it is exposed to the ambient air existing in the reference-gas bore or passage 8. An output signal indicative of an electromotive force induced between the measuring and reference electrodes 4, 6 is fed to an external measuring device (not shown) through electrical leads (not shown) connected to the electrodes 4, 6, as is well known in the art.

After the outer and inner electrodes have been formed on the outer and inner surfaces of the solid electrolyte body, the outer measuring electrode (4) which is exposed to a measurement gas is covered with a ceramic coating layer in the form of a ceramic protective layer 10, as shown in FIGS. 1 and 2. This ceramic protective coating layer (10) is provided to protect the electrode layer (4) from direct exposure to the measurement gas, and thereby improve the durability or life expectancy of the electrode. Generally, the ceramic coating layer (10) is formed by spraying molten particles of a selected ceramic material with various spraying methods, in particular, with a plasma or flame spraying method. In a plasma spraying method, which is preferably used, molten particles of a selected ceramic material, usually, spinel ($Al_2O_3 \cdot MgO$) are sprayed with a plasma flame of $Ar/N_2$ or $N_2/H_2$, over the electrode, so that the electrode is covered with a ceramic coating layer of the selected ceramic material. While the outer measuring electrode (4) should be covered with the ceramic coating layer (10), it is not always necessary to cover the inner reference electrode (6) with such a ceramic protective layer.

The solid electrolyte body with the electrodes and the ceramic coating layer formed as described above is used as a principal part of the oxen sensing element, which is finally incorporated in an oxygen sensor. Before or after the sensing element or oxygen sensor is produced, the solid electrolyte body with the electrodes and the ceramic coating layer is heat-treated in a reducing atmosphere according to the invention, with a result of reducing a portion of the electrode which is adjacent to the ceramic coating layer and which has been oxidized or fused during formation of the ceramic coating layer. The reduction of the oxidized or fused portion of the electrode contributes to an increase in specific surface area of the metallic electrode, and to generation of smaller pores in the structure of the electrode, whereby the operating response of the oxygen sensor is effectively ameliorated for the entire range of temperature of the measurement gas.

The above-indicated heat treatment may be effected in any reducing atmosphere which contains a gas commonly used for a reducing operation. In particular, it is advantageous to use an atmosphere containing hydrogen, carbon monoxide, or a mixture thereof, or a cracking gas.

The heat treatment according to the invention may be accomplished generally at a temperature within a range from 700° C. to 900° C. In this temperature range, the effect of the heat treatment is prominent. If the heat treatment temperature is lower than 700° C., the reducing effect of the heat treatment is decreased, and consequently the heat treatment has a reduced effect on the improvement in the response of the sensor at a relatively high temperature of the measurement gas (e.g., exhaust gas from an engine). If the heat treatment temperature is higher than 900° C., on the other hand, the metallic material of the electrode such as platinum is fired to an excessive extent, and the heat treatment has a reduced effect on the improvement in the response at a relatively low temperature of the measurement gas.

In the heat treatment according to the invention, the portion of the ceramic coating layer covering the electrode to be exposed to the measurement gas is held at a temperature within the above-specified range, for a length of time sufficient to provide an intended result. It is difficult to limit the holding time comprehensively for the above temperature range. Generally, the heat treatment is continued for one-half hour to five hours. If the heat treatment is performed for a period within this time range and within the preferred temperature range indicated above, an outstanding effect on the improvement in the response of the sensor is expected.

The heat treatment according to the invention is preferably applied to the ceramic coating layer formed over the electrode on the solid electrolyte body, before the solid electrolyte body is processed into the sensing element. As previously indicated, however, the heat treatment may be effected on the sensing element which comprises the solid electrolyte body with the ceramic coating layer. Further, the oxygen sensor incorporating the sensing element may be subjected to the heat treatment according to the invention. At any rate, the heat treatment should be achieved so as to reduce the electrode underlying the ceramic coating layer.

As is apparent from the foregoing description, the present invention provides an improved process of manufacturing an oxygen sensor which is excellent in operating response over the full range of temperature of a measurement gas such as an exhaust gas. In the case where the instant oxygen sensor with an improved operating response is employed for controlling a combustion condition of an engine of an automotive vehicle, the exhaust gas from the engine may be effectively purified with a high purification ratio by controlling an air-fuel ratio of the air-fuel mixture for the engine, in response to the detected oxygen concentration in the exhaust gas. Further, the heat treatment according to the invention also contributes to improvement of a value "$\lambda$" of the exhaust gas (a ratio of an air-fuel ratio of the exhaust gas over an air-fuel ratio of the stoichiometric exhaust gas), even when the exahust gas temperature is comparatively low. Namely, the instant oxygen sensor is capable of controlling the air-fuel ratio of the air-fuel mixture for the engine, so that the value $\lambda$ of the exhaust gas is held within a very narrow range near "1" (one), that is, the exhaust gas may be highly purifed, even when the exhaust gas temperature is relatively low, for instance, immediately after a cold engine has been started. In addition, the durability of the oxygen sensor is improved since it is always exposed to the highly purified exhaust gas as indicated above.

While the present invention has been described in connection with an ordinary type of oxygen sensor with a solid electrolyte body and plurality of electrodes as shown in FIGS. 1 and 2, the principle of the invention is also applicable to the manufacture of various other types of oxygen sensors. For example, the process of the invention is applicable to: a sensor having a heating element incorporated in the solid electrolyte body or in the sensing element; a lean-burn sensor which is capable of detecting a lean-burned exhaust gas which is produced in the combustion of a fuel-lean air-fuel mixture; and an oxygen sensor which includes an electrochamical pumping cell, as well as the electrochemical sensing cell as illustrated in the accompanying drawing.

To further clarify the concept of the present invention, several examples of the invention will be described. However, it is to be understood that the invention is by no means confined to the details of the these examples, but may be embodied with various changes, alterations, modifications and improvements which may occur to those skilled in the art, without departing from the spirit and scope of the invention defined in the appended claims.

EXAMPLES

Outer and inner electrodes of platinum were formed on corresponding outer and inner surfaces of tubular solid electrolyte bodies made of partially stabilized zirconia (PSZ), by electroless plating, or by means of thermal decomposition of chloroplatinic acid ($H_2PtCl_6$). Subsequently, a ceramic coating layer of spinel was formed over the outer electrode, by plasma spraying. Thus, there were prepared various sensing elements with their outer electrode covered with the spinel coating layer as illustrated in FIG. 1.

The individual sensing elements were then subjected to heat treatments under different conditions (treating atmosphere and temperature) indicated in Table 1. The sensing elements were held at the indicated maximum temperatures for three hours.

The heat-treated sensing elements were built in respective oxygen sensors, and were placed in operating conditions, namely, exposed to exhaust gases at 350° C. and 850° C., in order to evaluate their operating responce ($T_{RL}$) at these relatively low and high temperatures. The measurement of the response times are indicated in Table 1.

It is understood that the evaluation of the response is increased as the response time (msec) is reduced. Each value of the response time indicated in the table was a length of time between the moment when the measurement gas was changed from a rich-burned exhaust gas (produced in combustion of an air-fuel mixture containing a relatively large amount of fuel) into a lean-burned exhaust gas (produced in combustion of an air-fuel mixture containing a relatively large amount of air), and the moment when the obtained electromotive force was changed from 600 mV to 300 mV.

TABLE 1

| No. | Electrode formed by | Heat-Treatment Atmosphere | Heat-Treatment Temperature (°C.) | 350° C. $T_{RL}$ (msec) | 850° C. $T_{RL}$ (msec) |
|---|---|---|---|---|---|
| 1 | Plating | — | — | 70 | 35 |
| 2 | " | Air | 800 | 80 | 35 |
| 3 | " | $H_2$ (dry) | 650 | 65 | 35 |
| 4 | " | " | 700 | 60 | 25 |
| 5 | " | " | 800 | 45 | 18 |
| 6 | " | " | 900 | 53 | 15 |
| 7 | " | " | 950 | 84 | 13 |
| 8 | " | $H_2$ (wet) | 800 | 66 | 27 |
| 9 | " | 10% CO* | 800 | 58 | 24 |
| 10 | Thermal decomposition of platinic acid | — | — | 50 | 29 |
| 11 | Thermal decomposition of platinic acid | Air | 800 | 50 | 30 |
| 12 | Thermal decomposition of platinic acid | $H_2$ (dry) | 800 | 45 | 17 |

*Cracking gas of butane containing 10% CO

It will be understood from Table 1 that the sensing elements (Examples Nos. 3–9 and 12) whose ceramic coating layer was heat-treated in hydrogen or an atmosphere containing 10% CO, according to the invention, demonstrated better results of response at 350° C. and 850° C., than the sensing elements (Examples Nos. 1 and 10) whose coating layer was not heat-treated, and the sensing elements (Examples Nos. 2 and 11) whose coating layer was heat-teated in air.

What is claimed is:

1. A process of manufacturing an oxygen sensor having an oxygen sensing element which includes an oxygen-ion conductive solid electrolyte body, a plurality of electrodes on the solid electrolyte body, and a porous ceramic coating layer which covers at least one of the electrodes which is disposed on a measurement gas side of the sensor, such that said one of the electrodes is exposed to the measurement gas through said porous ceramic coating layer, the process comprising the steps of:
    forming said porous ceramic coating layer so as to cover at least said at least one of the electrodes; and
    heat-treating at least a portion of the porous ceramic coating layer covering said at least one electrode, said heat-treating occuring in a dry hydrogen atmosphere.

2. A process according to claim 1, wherein said solid electrolyte body is a tubular or planar body comprising a zirconia ceramic.

3. A process according to claim 1, wherein said electrodes comprise an element selected from the group of materials consisting of the platinum group and an electrically conducting material which contains as a major component thereof an element selected from said platinum group.

4. A process according to claim 1, wherein said porous ceramic coating layer is formed by spraying molten ceramic material particles.

5. A process according to claim 4, wherein said porous ceramic coating layer is formed by a plasma spraying technique.

6. A process according to claim 1, wherein the heat-treating step is effected at a temperature of 700°–900° C.

7. A process according to claim 1, wherein said heat-treating step is effected for a period of time of 0.5–5 hours.

8. A process of manufacturing an oxygen sensor having an oxygen sensing element which includes an oxygen-ion conductive solid electrolyte body, a plurality of electrodes on the solid electrolyte body, and a porous ceramic coating layer which covers at least one of the electrodes which is disposed on a measurement gas side of the sensor, such that said one of the electrodes is exposed to the measurement gas through said porous ceramic coating layer, the process comprising the steps of:
    forming said porous ceramic coating layer so as to cover at least said at least one of the electrodes; and
    heat-treating in a dry hydrogen atmosphere at least a portion of the porous ceramic coating layer covering said at least one electrode, said heat-treating occuring at a temperature of 700°–900° C. for a period of time of 0.5–5 hours.

9. A process according to claim 8, wherein said solid electrolyte body is a tubular or planar body comprising zirconia ceramics.

10. A process according to claim 8, wherein said electrodes comprise an element selected from the group of materials consisting of the platinum group and an electrically conducting material which contains as a major component thereof an element selected from said platinum group.

11. A process according to claim 8, wherein said porous ceramic coating layer is formed by spraying molten ceramic material particles.

12. A process according to claim 11, wherein said porous ceramic coating layer is formed by a plasma spraying technique.

* * * * *